United States Patent [19]

Takahashi et al.

[11] Patent Number: 5,164,973
[45] Date of Patent: Nov. 17, 1992

[54] PROJECTION DETECTING APPARATUS FOR COMPUTER TOMOGRAPHY

[75] Inventors: Tetsuhiko Takahashi, Soka; Manabu Nakagawa, Kanagawa; Hideji Fujii; Minoru Yoshida, both of Tokyo, all of Japan

[73] Assignee: Hitachi Medical Corporation, Tokyo, Japan

[21] Appl. No.: 637,638

[22] Filed: Jan. 4, 1991

[30] Foreign Application Priority Data

Jan. 5, 1990 [JP] Japan .................................. 2-000341

[51] Int. Cl.$^5$ .............................................. H05G 1/60
[52] U.S. Cl. ........................................ 378/19; 250/367
[58] Field of Search .......................... 378/19; 250/367

[56] References Cited

U.S. PATENT DOCUMENTS 4,176,279 11/1979 Schwierz et al. ...................... 378/19
4,725,734 2/1988 Nishiki .................................. 378/19
4,982,096 1/1991 Fujii et al. ............................ 250/367

*Primary Examiner*—Craig E. Church
*Attorney, Agent, or Firm*—Antonelli, Terry, Stout & Kraus

[57] ABSTRACT

A projection detecting apparatus for use in a third generation X-ray computer tomography includes an X-ray source and a detector array both mounted on a rotatable gantry for detecting X-ray projections of an object under inspection sequentially at a plurality of angles of the gantry, respectively. The detector array is formed by disposing consecutively a plurality of detector element blocks each constituted by a photodiode array and a scintillator array laminated together. The element blocks are so disposed as to be asymmetric to the center line of a fan-like radiation beam which line extends through the position of the X-ray source and the center of rotation of the gantry.

8 Claims, 4 Drawing Sheets

F I G. 2
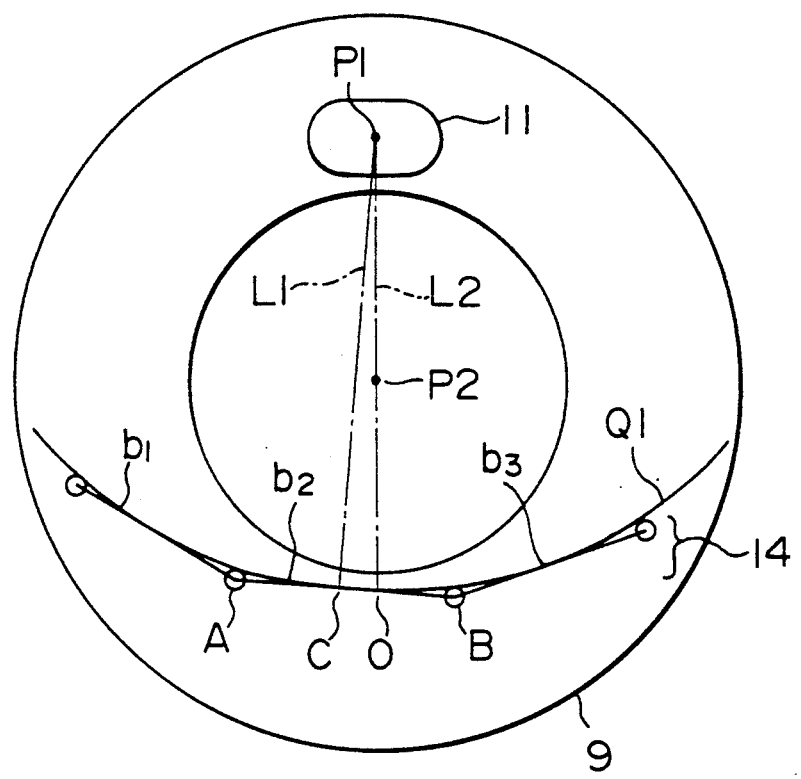
F I G. 3
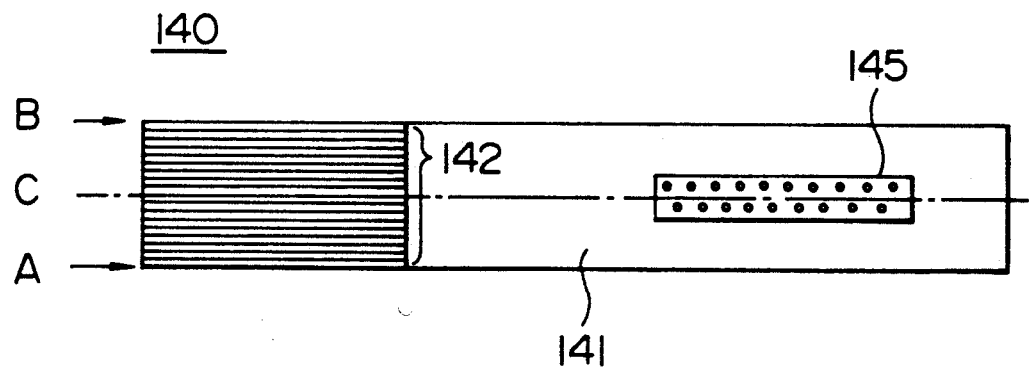

PROJECTION DETECTING APPARATUS FOR COMPUTER TOMOGRAPHY

BACKGROUND OF THE INVENTION

The present invention relates generally to a projection detecting apparatus including an array type radiation detector set for detecting projections generated by radiation. More particularly, the invention is concerned with a projection detecting apparatus which can be advantageously or profitably employed in an X-ray computer tomography system for medical use.

As the X-ray detecting apparatus for the X-ray computer tomography (CT), there has been proposed in recent years a structure which comprises scintillator elements which emit light photons in response to X-rays and photodiodes serving as photoelectric conversion elements for converting the light photons into electric signals.

In the case of the X-ray computer tomography or CT system known heretofore in the art, a large number of detectors are arrayed on and along a circular arc, whereby X-ray projections of an object under inspection are sequentially detected in the different directions. In U.S. patent application Ser. Nos. 293,764 filed Jan. 5, 1989 in the name of the present inventors and others as joint applicants and U.S. Pat. No. 4,725,734, there is disclosed element blocks each constituted by a plurality of X-ray detector elements (hereinafter also referred to as detector elements or simply as elements) which are arrayed linearly. A plurality of such planar element blocks are disposed closely to one another along a circular arc having a center at which an X-ray source is disposed, whereby a detector array of a generally arcuate configuration as a whole is realized. With the aid of such element array, the X-ray projections of an object under inspection are detected.

A problem of the detector array constituted by a plurality of the element blocks such as mentioned above can be seen in that the characteristics of the elements located at the ends of each block frequently differ slightly from those of the other elements. In the so-called third generation X-ray computer tomography, non-uniformity in the sensitivity among the detector elements provides a cause for generation of ring artifact on the tomogram reconstituted. Consequently, when the projection detecting apparatus of the block structure mentioned above is used, frequently the ring artifacts appear at the locations on the tomogram which correspond to the interblock joints.

Parenthetically, relationship between the characteristics of the detector element itself and the ring artifact is discussed in Dennis L. Parker et al: "Design constraints in computed tomography: A theoretical review", Med. Phys. 9(4), July/August 1982, pp. 531-539.

As the attempts for reducing the ring artifacts mentioned above, there have been proposed a method for improved securing of the detector blocks (reference may be made, for example, to JP-A-64-88178) and a method for improving the inter-block joints (see, for example, JP-A-63-151886).

It has however be found that notwithstanding of the attempts and approaches mentioned above, the nonuniformity in the sensitivity among the elements which causes the ring artifact to appear can not satisfactorily be eliminated. Above all, in the case of the structure in which a plurality of planner element blocks are employed, as described previously, the detector elements are not arrayed on a circular arc but on and along the sides of a polygon in the strict sense. Accordingly, considering the detector elements located on a given one of the element blocks closer to both ends of that one block, respectively, it is apparent that the surfaces of these elements on which the X-ray are incident do not extend perpendicularly to the direction of the incident X-rays, as a result of which the sensitivity of the elements under consideration is lower in general when compared with that of those elements disposed in the vicinity of the center of the block. In this conjunction, it is further to be noted that each of the element blocks includes a semiconductor plate in which a plurality of photodiodes are implemented in the form of an array, wherein each of the photodiodes is assigned to each of the individual detector elements. Due to such configuration of the photodiode array, dark currents generated in the photodiodes located at both ends of the element block tend to become greater when compared with those located at inner sides to the former. For these reasons, it is safe to say that the detector elements located closer to the ends of each element block and among others those located at both outermost ends of each element block exhibit singularly deviation or error in the sensitivity.

SUMMARY OF THE INVENTION

Accordingly, it is an object of the present invention to provide a projection detecting apparatus for a computer tomography (CT) in which the ring artifact is made difficult to occur on a reconstructed image notwithstanding of the nonuniformity in sensitivity ascribable inherently to the polygonal array of the detector elements.

Another object of the present invention is to provide a projection detecting apparatus for the CT in which singular occurrence of the sensitivity deviation in the detector elements located at o close to both ends of the element blocks can be suppressed to a minimum.

In view of the above and other objects which will become more apparent as description proceeds, there is provided according to an aspect of the present invention a projection detecting apparatus for a CT system which comprises a gantry having a cavity formed at a center portion thereof for allowing an object for inspection to be inserted therein and driven rotationally, a radiation source for emitting a radiation beam of a sector- or fan-like shape toward the object under inspection, and a plurality of planar detector element blocks arrayed closely to one another substantially along a circular arc having a center coinciding with the position of the radiation source and each including a plurality of radiation detecting elements, wherein the plurality of the detector element blocks are so disposed as to be asymmetrical relative to a line which passes through the position of the radiation source and the center of rotation of the gantry (this line will herein-after be referred to as the fan beam center line). In other words, the individual planar element blocks are so arrayed that the positions of the apexes of a polygon defined by a plurality of the planar element blocks disposed closely to one another, i.e. the positions of the ends of the individual element blocks do not superpose or overlap one another, when the element block array is folded up along the fan beam center line (also referred to as the center line for measurement).

More specifically, the plural blocks are so disposed that the center line for measurement intersects one element block at an intermediate position which is neither the center position nor the end position of the one element block.

By virtue of the asymmetrical disposition of the detector element blocks mentioned above, projections of the object under inspection are detected at plural rotation angles of the gantry, respectively, wherein upon reconstruction of a tomograph through computer tomography processing, the ring artifact ascribable to the detector elements positioned at both ends of each element block and exhibiting significant sensitivity deviation are prevented from superposing each other. Thus, the intensity of the ring artifact can be reduced significantly.

According to another aspect of the present invention, each of the element blocks mentioned above includes in a laminated structure a scintillator array for converting the radiation rays into optical photons or light rays and a semiconductor plate having a photodiode array formed therein for converting the light rays into electric signals, wherein the width of the substrate (the width as viewed in the direction of the array) is selected slightly greater than the width of the semiconductor plate. More specifically, in order to ensure that no deviation in the element pitch takes place at the joints of the blocks, a range is determined for the value of the width of the substrate. It is preferred that the width b of the substrate should lie within a range given by $$a*n*(r+d)/r > b > a*c \qquad (1)$$

where r represents the radius of the circular arc, d represents a total thickness of the scintillator array and the semiconductor plate, a represents the element pitch and n represents the number of detector elements in each of the element blocks. In the range mentioned above, substantially no deviation occurs in the pitch of the whole elements. Further, because the end face of the substrate projects slightly beyond that of the semiconductor plate at the end portions of each element block, there can be prevented the possibility of impurities being deposited onto the end surfaces of the semiconductor plate in the course of assembling the projection detecting apparatus for thereby causing the dark current to increase singularly only at the photodiodes located at the ends of the element block, respectively.

BRIEF DESCRIPTION OF THE DRAWINGS

FIG. 2 is a diagram for illustrating the concept underlying a projection detecting apparatus according to an exemplary embodiment of the invention;

FIG. 3 is a top plan view of an element block employed in the apparatus shown in FIG. 2;

DESCRIPTION OF THE PREFERRED EMBODIMENTS

Figure 1:
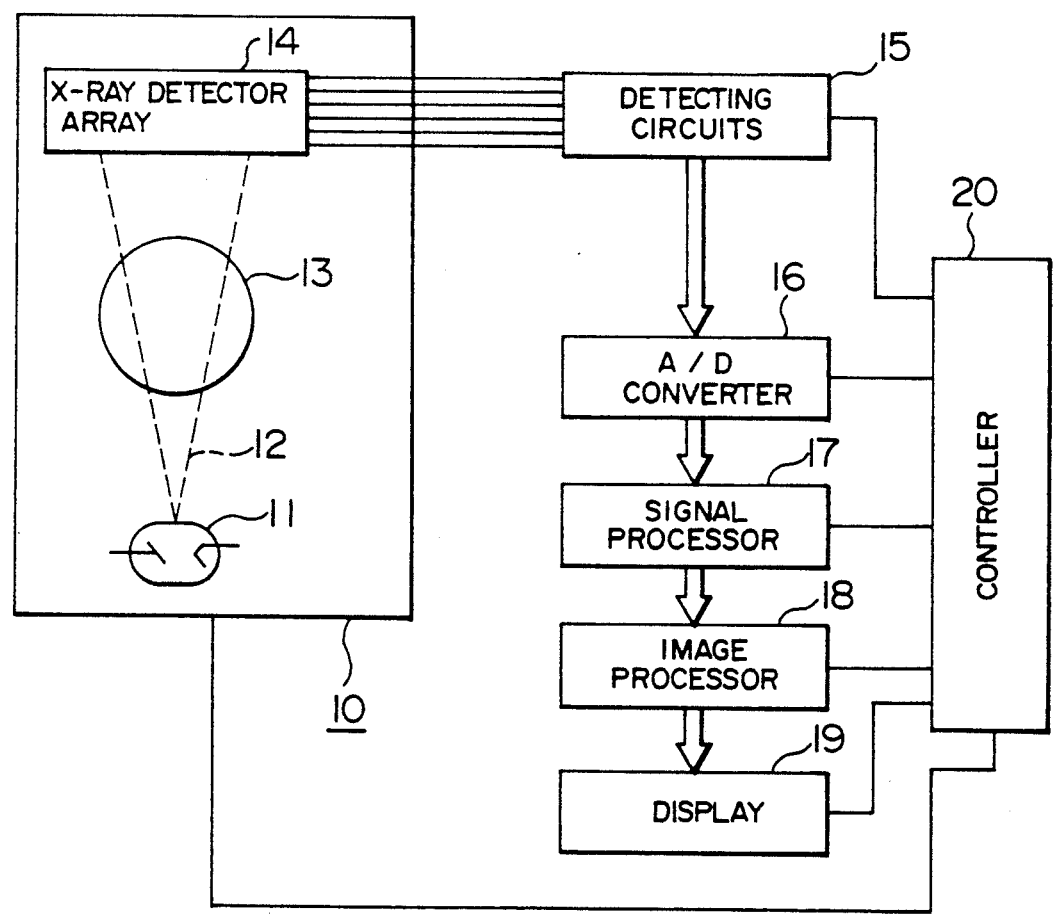
FIG. 1 is a block diagram showing a general arrangement of an X-ray computer tomography (CT) system to which the present invention can be applied.

FIG. 1 shows in a block diagram an X-ray computer tomography or CT system to which the present invention is to be applied. Referring to the drawings, a projection detecting apparatus generally denoted by a numeral 10 is adapted to detect successively the X-ray projections of an object under inspection. More specifically, an X-ray beam emitted by an X-ray tube 11 is transmitted through the object 13 to be detected by an X-ray detector array 14 through conversion of X-ray intensity signals into electric current signals.

The electric current signal outputted from the projection detecting apparatus 10 is converted to a voltage signal by detection circuits 15. The analogue voltage signal is converted to a digital signal by an analogue-to-digital (A/D) converter 16. The digital signal is then supplied to a signal processor 17 to undergo signal correction such as sensitivity correction of the X-ray detector array 14 and offset correction of the detection circuits 15 on a channel-by-channel basis. On the basis of a set of these corrected data, there can be obtained one-dimensional projection data.

The X-ray CT system according to the illustrated embodiment of the invention belong to what is called the third generation CT system in which the X-ray tube 11 and the detector array 14 are rotated simultaneously to derive lots of projection data. On the basis of these data, a tomogram is reconstructed. Arithmetic operation required for the reconstruction is performed by an image processor 18. The tomogram reconstructed by the image processor 18 is finally displayed on a display 19. It should finally be added that the individual constituent parts of the X-ray CT system mentioned above is controlled by a controller 20.

FIG. 2 is a schematic diagram showing a structure of the projection detecting apparatus 10 according to an embodiment of the present invention. A gantry 9 is formed with an air gap or cavity at a center portion which is of a sufficiently large size to allow a living body (i.e. the object for inspection) to be inserted therein while it lies on a bed. Mounted in the gantry 9 is an X-ray tube 11 for emitting an X ray beam of a sector- or fan-like form and a detector array 14 constituted by a great number of X-ray detector elements. Ideally, these X-ray detector elements should be arrayed on and along a circular arc $Q_1$ having a center at the position $P_1$ of the X-ray source constituted by the X-ray tube 11. In the case of the illustrated embodiment of the invention, however, a specific number of X-ray detecting elements are realized integrally in the form of one element block constituting a linear element array. A plurality of these element blocks are arrayed closely to one another in such manner that an element array disposed along the circular arc $Q_1$ can approximately be realized. In actuality, however, the detector element array assumes such a polygonal shape as represented by segments $b_1$, $b_2$ and $b_3$ in FIG. 2. At this juncture, it should be mentioned that although only three element blocks $b_1$, $b_2$ and $b_3$ are shown, this is merely for the purpose of facilitating the illustration. In the practical projection detecting apparatus, such element blocks are provided in a greater number, e.g. ten or more.

FIG. 3 is a top plan view showing one element block according to the instant embodiment of the invention. Referring to the drawings, there are deposited on one end portion of a substrate 141 constituted by a rectangular insulation plate thereof a silicon wafer having a photodiode array formed therein and a scintillator plate which is cut into rod-like scintillator elements (also referred to as scintillator rods) disposed in positional correspondence to the individual photodiodes, respectively. In this manner, there is formed on the substrate 141 a detector array 142 which includes a plurality of detector elements (eighteen elements in the case of the illustrated embodiment) each constituted by a pair of the photodiode and the scintillator rod. Parenthetically, it should be added that separators are inserted between the adjacent scintillator rods so that the individual detector elements are optically and radiatively separated from one another. Signal lines (not shown) extend from the photodiodes of the individual detector elements, respectively, to be connected to a connector 145 for establishing electrical connection with the detecting circuits.

Now, turning back to FIG. 2, the gantry 9 is rotationally driven by a motor (not shown) about the center axis extending through a position $P_2$, in the course of which the projections of the object under inspection are detected by the detector array 14 successively at plural different angles, respectively. In the following, a line $L_2$ which interconnects the position $P_1$ of the X-ray source constituted by the X-ray tube 11 and the position $P_2$ will be referred to as the fan beam center line which may also be termed the center line for measurement. The illustrated embodiment of the invention is characterized in that the intersection 0 between the element block $b_2$ and the fan beam center line $L_2$ is slightly offset or deviated from the center C of the element block $b_2$. By virtue of such arrangement, the apexes of a polygon formed by the arrayed element blocks (i.e. end positions of the individual element blocks typified by points A and B) are positioned asymmetrically with reference to the fan beam center line $L_2$. In this conjunction, it should be mentioned that in the case of the third generation X-ray CT system in which the X-ray source emitting a fan-like X-ray beam is rotated together with the detector element array to detect the projections successively at different angles of rotation, whereon a tomogram is reconstructed from a plurality of projections, there makes appearance on the reconstructed image a ring which is inscribed in common by straight lines interconnecting the detector elements exhibiting deviation in sensitivity and the X-ray source at the rotational angles, respectively. This ring is referred to as the ring artifact. In this connection, it is further noted that in the case of the polygonal detector element array composed of the linear element blocks, the sensitivity deviation mentioned above becomes more significant in these elements that are disposed more closely to the apexes of the polygon or the ends of the element blocks, to say in another way. However, by virtue of the asymmetrical disposition shown in FIG. 2, the ring artifact ascribable to the sensitivity deviation of the detector element located closest to the apex A is not superposed on the ring artifact due to the sensitivity deviation of the detector element located closest to the apex B, whereby intensity level of the ring artifact is reduced as a whole.

More specifically, the position of the block $b_2$ is so determined that the intersection point 0 assumes a position closer to at least the block center C than the end B of the element block, the reason for which will be described by reference to FIG. 4. This figure shows the results obtained from scrutinization of the influences exerted on the image by the nonuniformity or deviation in the sensitivity of the detector array. More specifically, in FIG. 4, there is taken along the ordinate the intensity of the ring artifact produced by the detector element exhibiting predetermined magnitude of the sensitivity deviation of those constituting the detector array, while the position of the detector element having the abovementioned sensitivity deviation is taken along the abscissa in terms of the number of the elements counted starting from the center line for measurement.

Figure 4:
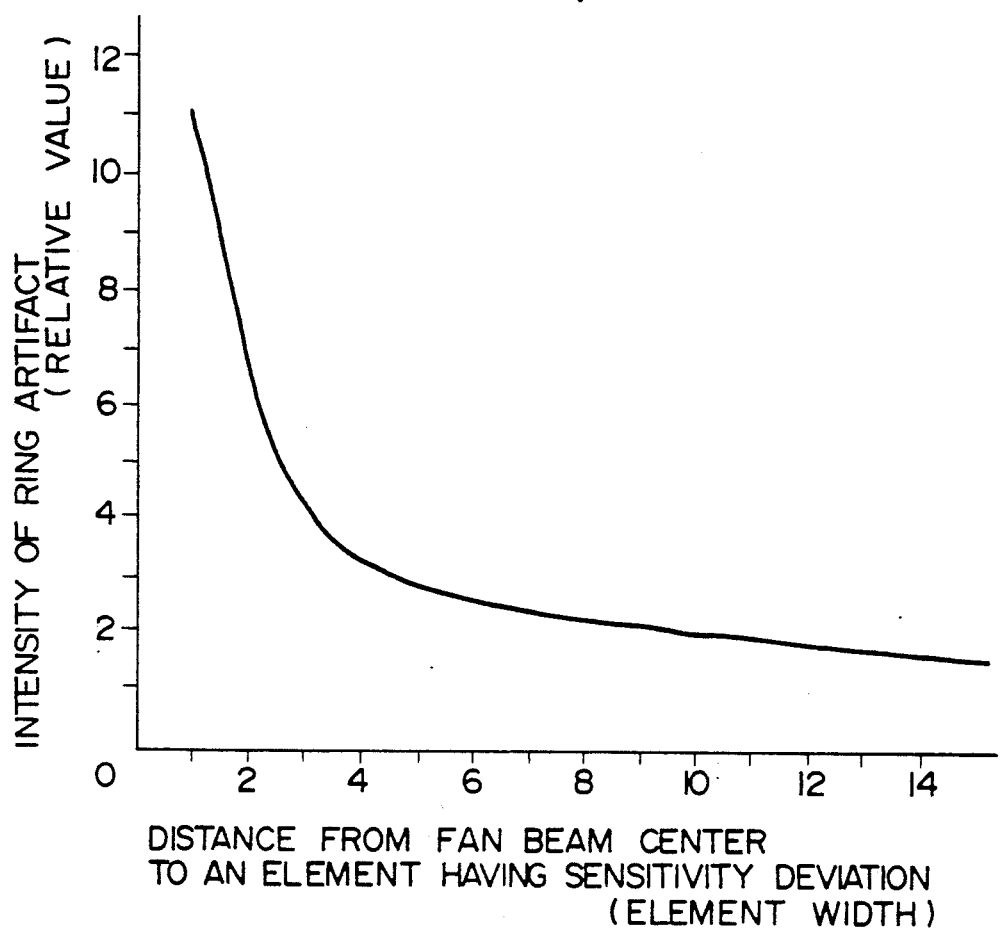
FIG. 4 is a characteristic diagram for illustrating a relation between a position of a detector element exhibiting sensitivity deviation and intensity of a ring artifact.

It can be seen from FIG. 4 that even when the sensitivity deviation is constant over the detector elements, the intensity of the ring artifact appearing on the image differs from one to another detector element in dependence on the position thereof and that the sensitivity deviation of the detector element affects more seriously the artifact as that detector element is located more closely to the center line for measurement. Consequently, in the case of the arrangement shown in FIG. 2, more significant ring artifact will make appearance due to the sensitivity deviation of the element positioned in the vicinity of the point B as the position of the point 0 becomes closer to the point B. Thus, the point 0 should preferably be positioned closer to the block center C than to the point B.

Further, FIG. 4 shows that the intensity of the ring artifact decreases abruptly within a range from the center to the fifth element while decreasing gently outside of the above range. Accordingly, when the number of the elements of one block, i.e. the number of the elements existing between the points A and B is represented by n with the number of the elements located between the points 0 and C being represented by $\Delta n$, it is preferred that the following condition be satisfied:
$OB = n/2 - \Delta n \geq 5$
and hence $$\Delta n \leq n/2 - 5 \qquad (2)$$

Further, it can be seen in FIG. 4 that for the element distanced from the center line for measurement by a space corresponding to more than ten elements, inclusive, the intensity of the ring artifact decreases to 1/5 or less when compared with that of the center element, to more advantageous effect. In this case, the following condition will have to be met.

$$\Delta n \leq n/2 - 10 \qquad (3)$$

On the other hand, in order to avoid the superposition of the ring artifacts ascribable to the detector elements located at both ends of the block, as mentioned hereinbefore, the following condition should be met.

$OA - OB \geq 3$
and hence $$\Delta n \geq 1.5 \qquad (4)$$

Figure 5:
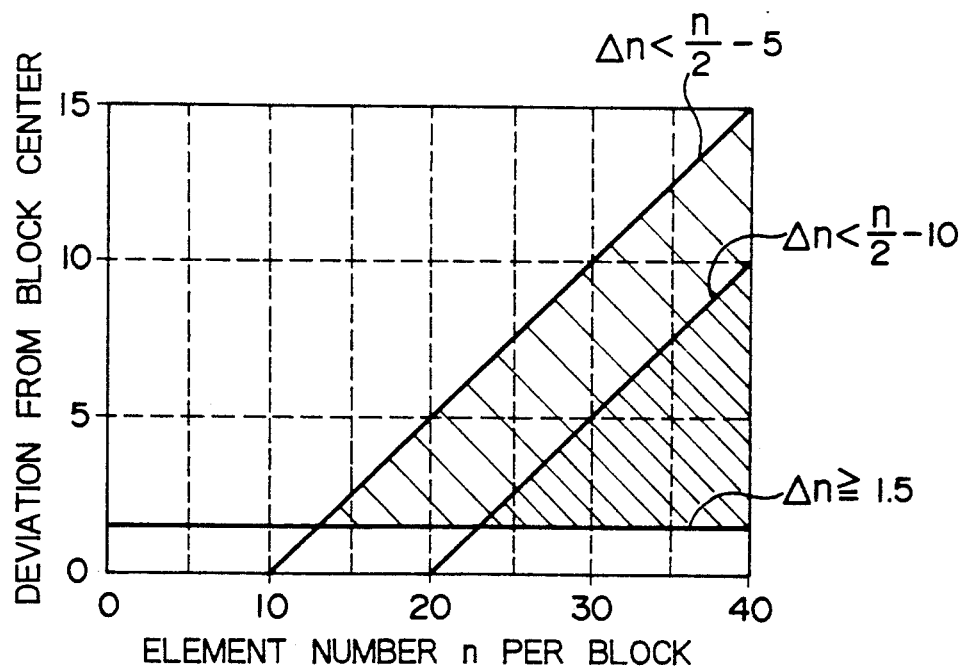
FIG. 5 is a two-dimensional graph for illustrating ranges of appropriate positions of detector element blocks and the number of the detector elements.

FIG. 5 is a two-dimensional graph in which the ranges given by the expressions (2), (3) and (4) are shown with the number n of the elements of one block being taken along the abscissa. As can be seen from this graph, it is preferred that the number n of the elements of one block is fourteen or more and that the center line $L_2$ for measurement passes through an intermediate position which is distanced from the block center C by at least 1.5 element widths while distanced from the block end B or A by at least 5 element widths. More preferably, the number n of the elements should be 24 or more, and the center line $L_2$ should pass through an intermediate position distanced by 1.5 element widths or more from the block center C and by 10 element widths or more from the end B or A of the block. However, when the number n exceeds 48, the sensitivity deviation itself of the elements positioned in the vicinity of the block ends increases. Accordingly, it is most preferred that the number n lies within a range of 24 to 48.

Figure 6:
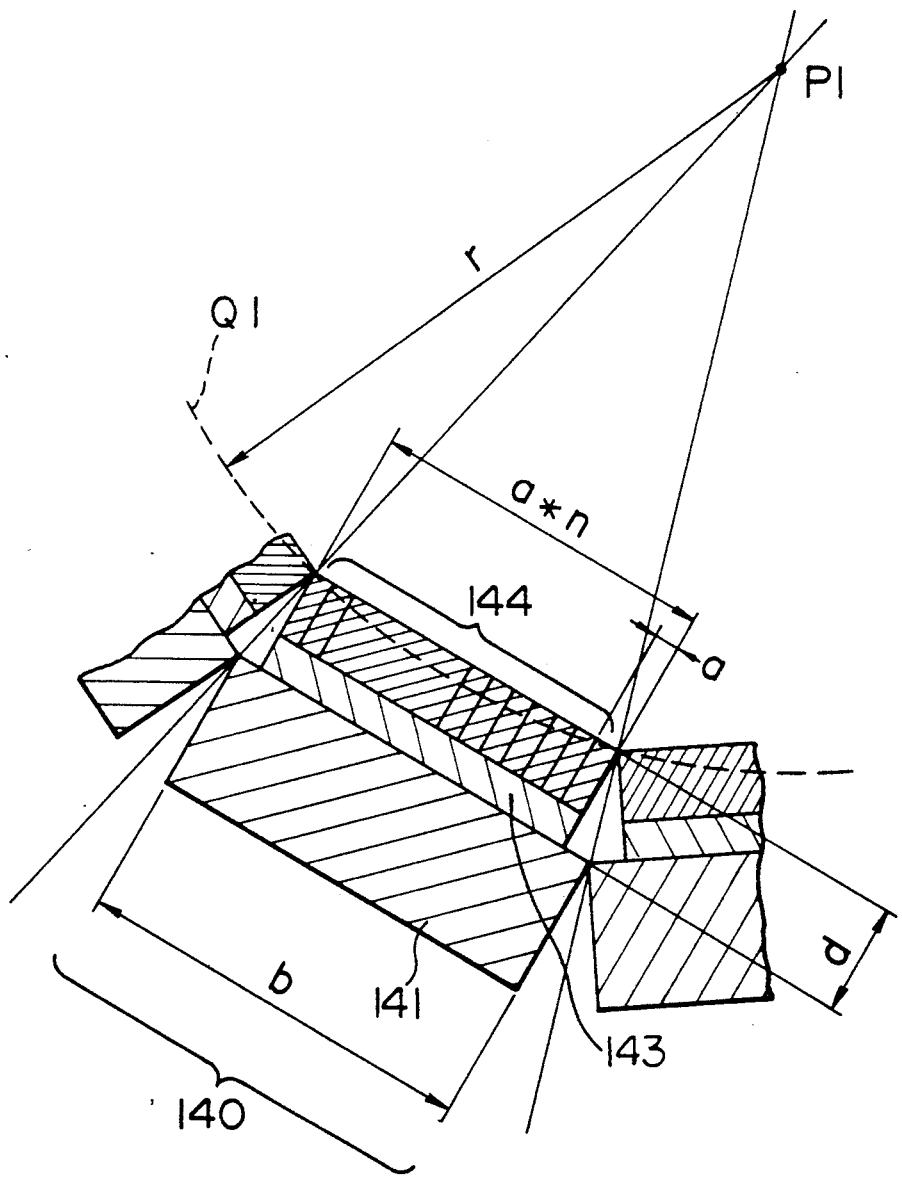
FIG. 6 is a sectional view of a detector element block.

FIG. 6 is a sectional view of an element block used in the apparatus according to the illustrated embodiment of the invention. Deposited in lamination on a substrate 141 of an insulation material a silicon plate 143 having a photodiode array formed therein and a scintillator array 144 cut on an element basis. The substrate 141 has a width b which is slightly greater than that of the photodiode array and the scintillator array. In other words, the end faces of the substrate 141 projects slight beyond those of the silicon plate 143, respectively. This structure is effective for suppressing or reducing the possibility of impurities being deposited on the side surfaces of the silicon plate 143 in the packaging process for assembling the element block in the projection detecting apparatus. In other words, dark currents in the photodiodes of the elements located at the ends of the block can be prevented from increasing. However, limitation is naturally imposed on the extent of projection of the substrate in order to prevent deviation or error of the element pitch from taking place at the joints between the element blocks arrayed along the circular arc $Q_1$. Accordingly, when the radius of the circular arc $Q_1$ is represented by r the element pitch is represented by a, the number of the element in one block is represented by n and when the total thickness of the scintillator array 144 and the silicon plate 143 is represented by d, the width of the substrate mentioned above should be so selected as to lie within a range given by the following expression.

$$a*n*(r+d)/r > b > a*n \quad (5)$$

By way of example, when
d = 1.5 mm, and
r = 1200 mm,
then
a*n*1.0013 > b > a*n.
Further, when
n = 24, and
a = 1.0 mm,
then
24.03 > b > 24.00

Thus, there can be realized such configuration of the block in which the end faces of the substrate protrude slightly at both ends of the block.

We claim:

1. A projection detecting apparatus for a computer tomography, comprising;
   a gantry having a space formed at a center portion for allowing an object for inspection to be inserted therein and driven rotationally around a predetermined position defining the center of rotation;
   a radiation source installed in said gantry for emitting a radiation beam of a fan-like shape toward and object;
   a detector array disposed in said gantry in opposition to said radiation source with said space for allowing insertion of said object being interposed between said detector array and said radiation source, for thereby detecting radial projections of said object at plural angles of rotation of said gantry, respectively;
   said detector array being constituted by a plurality of detector element blocks disposed in said gantry, said blocks being arrayed generally along a circular arc having a center at a position coinciding with that of said radiation source, each of said detector element blocks including a plurality of radiation detector elements disposed in the form of a linear array;
   said plurality of detector element blocks being disposed at positions asymmetrical to a fan beam center line which passes through the position of said radiation source and the center of rotation of said gantry; and
   said fan beam center line intersects one detector element block at a position distanced from the center position thereof by a space corresponding to at least 1.5 detector elements on said one detector element block to reduce ring artifacts generated at each boundary between adjacent blocks.

2. A projection detecting apparatus according to claim 1, wherein said plural detector element blocks including a substrate composed of an insulation plate, a semiconductor plate deposited on said substrate and having a photodiode array formed thereon, and an array of rod-like scintillator elements deposited on said semiconductor plate,
   wherein said substrate has end portions projecting slightly beyond those of said semiconductor plate.

3. A projection detecting apparatus for a computer tomography, comprising;
   a gantry having a space formed at a center portion for allowing an object for inspection to be inserted therein and driven rotationally around a predetermined position defining the center of rotation;
   a radiation source installed in said gantry for emitting a radiation beam of a fan-like shape toward said object;
   a detector array disposed in said gantry in opposition to said radiation source with said space for allowing insertion of said object being interposed between said detector array and said radiation source, for detecting radial projections of said objects at plural angles of rotation of said gantry, respectively;
   said detector array being constituted by a plurality of detector element blocks disposed in said gantry, said blocks being arrayed generally along a circular arc having a center at a position coinciding with that of said radiation source, each of said detector element blocks including a plurality of radiation detector elements disposed in the form of a linear array;
   said plurality of detector element blocks being so disposed that a fan beam center line passing through the position of said radiation source and said center of rotation of said gantry intersects one of said plural detector element blocks at a position slightly deviated from the center position of said one detector element block; and
   said fan beam center line intersects said one detector element block at a position distance from the center position thereof by a space corresponding to at least 1.5 detector elements on said one detector element block to reduce ring artifacts generated at each boundary between adjacent blocks.

4. A projection detecting apparatus according to claim 3, wherein said fan beam center line intersects said one detector element block at a position closer to the center position of said one detector element block than to an end position thereof.

5. A projection detecting apparatus according to claim 3, each of said plural detector element blocks including 14 or more radiation detector elements,
   wherein said fan beam center line intersects one of said detector element blocks at a position distanced from an end of said one element block by a space corresponding to 5 or more detector elements and distanced from the center position of said one element block by said space corresponding to at least 1.5 or detector elements.

6. A projection detecting apparatus according to claim 3, each of said plural detector element blocks including 24 or more radiation detector elements,
   wherein said fan beam center line intersects one of said detector element blocks at a position distanced from an end of said one element block by a space corresponding to 5 or more detector elements and distanced from the center position of said one element block by a space corresponding to 10 or more detector elements.

7. A projection detecting apparatus for a computer tomography, comprising:
   a gantry having a space formed at a center portion for allowing an object for inspection to be inserted therein and driven rotationally around a predetermined position defining the center of rotation;
   a radiation source installed in said gantry for emitting a radiation beam of a fan-like shape toward said object;
   a detector array disposed in said gantry in opposition to said radiation source with said space for allowing insertion of said object being interposed between said detector array and said radiation source, for detecting radial projections of said object at plural angles of rotation of said gantry, respectively;
   said detector array being constituted by a plurality of detector element blocks disposed in said gantry, said blocks being arrayed generally along a circular arc having a center at a position coinciding with that of said radiation source; and
   each of said detector element blocks including a substrate constituted by an insulation plate, a semiconductor plate deposited on said substrate and having formed therein a photodiode element array of an element pitch a, said array having n photodiode elements, and an array of rod-like scintillator elements deposited on said semiconductor plate, wherein said substrate has a width b which lies within a range given by $$a*n*(r+d)/r > b > a*n$$

where d represents a total thickness of said semiconductor plate and said rod-like scintillator array.

8. A projection detecting apparatus for computer tomography, comprising;
   a gantry having a space formed at a center portion for allowing an object for inspection to be inserted therein and driven rotationally around a predetermined position defining the center of rotation;
   a radiation source installed in said gantry for emitting a radiation beam of a fan-like shape towards said object;
   a detector array disposed in said gantry in opposition to said radiation source with said space for allowing insertion of said object being interposed between said detector array and said radiation source, for detecting radial projections of said object at plural angles of rotation of said gantry, respectively;
   said detector array being constituted by a plurality of detector element blocks disposed in said gantry, said blocks being arrayed generally along a circular arc having a center at a position coinciding with that of said radiation source, each of said detector element blocks including a plurality of radiation detector elements disposed in the form of a linear array;
   said plurality of detector element blocks being so disposed that a fan beam center line passing through the position of said radiation source and said center of rotation of said gantry intersects one of said detector elements located at an intermediate position rather than the detector elements located closest to the ends of said detector element block and at the center thereof; and
   said fan beam center line intersects said one detector element at a position distanced from the center of said detector element block by a space corresponding to at least 1.5 detector elements on said detector element block to reduce ring artifacts generated at each boundary between adjacent blocks.

* * * * *